United States Patent [19]
Ray

[11] Patent Number: 4,738,248
[45] Date of Patent: Apr. 19, 1988

[54] SURGICAL RETRACTORS

[75] Inventor: Charles D. Ray, Wayzata, Minn.

[73] Assignee: CeDaR Development Corp., Minnetonka, Minn.

[21] Appl. No.: 887,605

[22] Filed: Jul. 17, 1986

[51] Int. Cl.⁴ .............................................. A61B 17/02
[52] U.S. Cl. ..................................................... 128/20
[58] Field of Search ............. 128/20, 15, 16, DIG. 14, 128/21

[56] References Cited

U.S. PATENT DOCUMENTS

| | | | |
|---|---|---|---|
| 1,246,339 | 11/1917 | Smit | 128/16 |
| 3,035,838 | 5/1979 | Hirsch et al. | 128/20 |
| 3,203,829 | 8/1965 | Seyer et al. | 128/DIG. 14 |
| 4,151,838 | 5/1979 | Crew | 128/20 |
| 4,610,243 | 9/1986 | Ray | 128/20 |

OTHER PUBLICATIONS

Handbook of Chemistry and Physics, published by The Chemical Rubber Co. © 1966 and earlier years.
Van Nostrand's Scientific Encyclopedia, © 1976.
The Surgical Armamentarium, Title Page and p. 66, 1980.

Primary Examiner—William H. Grieb
Attorney, Agent, or Firm—Moore & Hansen

[57] ABSTRACT

A surgical retractor can be used in conjunction with an electro-surgical instrument without ensuring against the two coming too close together or touching when the surface of the tip of the retractor is electrically and thermally nonconductive and has a Rockwell C hardness of at least 55. The tip of the retractor may have a metal core which is provided with a hard, electrically insulating surface by sintering a ceramic such as aluminum oxide or zirconium oxide. Instead, the tip can be a piece of ceramic which is mounted onto a broad metal band by means of a short length of metal tubing.

15 Claims, 1 Drawing Sheet

SURGICAL RETRACTORS

BACKGROUND OF THE INVENTION

1. Field of the Invention

The invention concerns improvements in surgical retractors, the word "retractors" being here used to encompass any surgical tool that can be used to retract soft tissue within an incision, e.g., depressers, elevators, dissectors, and spatulas.

2. Description of the Related Art

Any incision for a surgical operation should be as narrow as possible, both to minimize post-operative trauma and also to leave the smallest possible scar. On the other hand, it sometimes is desirable to maintain an appreciable spacing between two surgical implements that have been inserted into the incision. For example, when using an electro-surgical instrument to produce highly localized heat for cutting or coagulating tissue, it usually is necessary to retract elements such as nerves, both to provide access and also to protect the retracted elements from the heat. Inasmuch as surgical retractors are metallic and conduct heat and electricity, great care must be exercised to maintain a spacing such that the electro-surgical instrument does not heat the retractor and thus damage tissue being contacted by the retractor.

Regardless of the size of the incision, there can be a problem in maintaining sufficient spacing between tissue to be cut or coagulated and other tissue. To illustrate, it sometimes is necessary to cauterize bleeding tissue located directly beneath a nerve which can be moved only a tiny distance without danger of being damaged, thus requiring the cauterizing instrument to be moved into close proximity to the retractor.

I suppose that consideration has been given to applying electrically and/or thermally insulating coatings such as "Teflon" or an enamel to surgical retractors, but such thoughts, if expressed, have probably been dismissed as impractical for reasons such as the need for any such coating to withstand sterilization procedures. Furthermore, any such coating would need to be resistant to abrasion inasmuch as surgical retractors often are used in conjunction with powered burs or with other steel instruments such as knives. In any event, I have never seen an electrically insulated surgical retractor of any kind nor one whose surface is resistant to cutting by a steel instrument.

SUMMARY OF THE INVENTION

The invention provides what I believe to be the first sterilizable surgical retractor that can be used in conjunction with an electro-surgical instrument without preventing the instrument from coming too close to or touching the retractor. The novel surgical retractor differs from those of the prior art in that its tip, which is to be inserted into an incision, is electrically and thermally nonconductive and has a Rockwell C hardness of at least 55. By "electrically nonconductive" is meant that the electrical resistivity at the surface of the tip is at least $10^3$ ohms/cm$^2$, preferably at least $10^6$ ohms/cm$^2$. By "thermally nonconductive" is meant that the thermal conductivity is not substantially greater than that of a typical ceramic.

Even if the tip of the novel surgical retractor were not electrically or thermally conductive, I believe it to be the first to have the aforementioned hardness, and this alone makes it more useful in conjunction with a bur or other instrument that might damage the surface of an ordinary surgical retractor. Also believed to be novel is a sterilizable surgical retractor, the tip of which has an electrically and/or thermally nonconductive surface.

Like most surgical retractors of the prior art, the novel surgical retractor preferably has a broad band and may have one or more teeth or spikes at the end of its tip to permit it to be used as a force-fulcrum retractor. The broad band of a force-fulcrum retractor may be shaped so that its central portion rests flat against the patient's body near the incision. In preferred surgical retractors of the invention, the metal or other material of the broad band is sufficiently malleable to be bent by hand to a desired shape while being sufficiently stiff to hold that shape against a retractile force applied to the other end of the band to pull the muscles and other tissue away from the center of an incision. Force-fulcrum surgical retractors having malleable bands are disclosed and claimed in my pending U.S. application Ser. No. 731,025, filed May 6, 1985 now U.S. Pat. No. 4,610,243, issued Sept. 9, 1986. As there taught, a preferred material for the malleable band is annealed 304 soft stainless steel having a thickness of about 1 mm.

The tip of the metal band of a surgical retractor, whether malleable or not, can be provided with a hard, electrically insulating surface by sintering a coating of a ceramic such as aluminum oxide, zirconium oxide, lithium aluminum silicate, or silicon nitride to cover at least one face of the tip. Preferably, the other face also is coated so that the surgeon does not need to be concerned which face is facing the instruments with which the retractor is being used. Instead of being applied by sintering, a thin layer of ceramic can be cast onto the tip or it can be precast and then cemented onto the tip. Regardless of the method of application, a ceramic coating preferably has a thickness from about 0.05 to 1.0 mm. A coating thinner than 0.05 mm might fracture too easily and might result in insufficient electrical puncture resistance. A coating thicker than 1.0 mm would be unneccessarily expensive and might be too bulky and/or irregular.

For economy, the tip may be a separate piece attached to the end of an otherwise conventional surgical retractor. When the tip is a separate piece, it may be completely ceramic.

BRIEF DESCRIPTION OF THE DRAWING

In the drawing, all figures of which are schematic.

Figure 1:
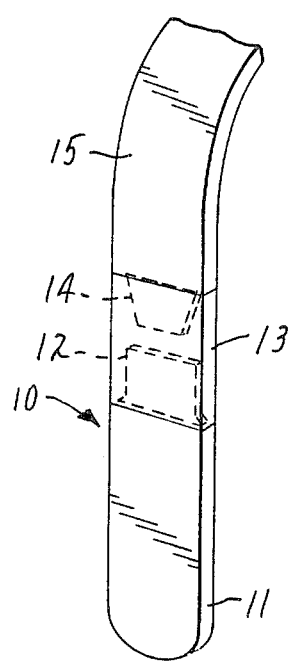
FIG. 1 is an isometric view of a first surgical retractor of the invention.

The surgical retractor 10 of FIG. 1 has a tip 11 in the shape of a spatula which is formed with a tongue 12 that fits into a short piece of metal tubing 13. Fitting into the other end of the tubing is a tongue 14 of a broad metal band 15. The tongues may be swaged into the tubing or may be secured by solder or by an adhesive such as a 2-part epoxy resin which is resistant to sterilizing temperatures. When using an adhesive, the tongues may be formed with ribs to provide a desired glue-line thickness as is known in the adhesive art.

The broad metal band 15 can be malleable as disclosed in the above cited U.S. Application Ser. No.

731,025. A malleable band may be bent to shape, then clamped to a rigid object such as a bony prominence to relieve the surgeon's or an assistant's hand. When the broad metal band is malleable, it may be flat for convenient shipment and then shaped as desired by the surgeon.

Figure 2:
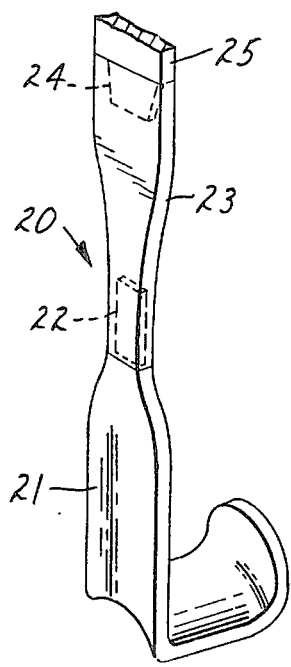
FIG. 2 is an isometric view of a second surgical retractor of the invention.

The surgical retractor 20 of FIG. 2 has a tip 21 in the shape of a nerve root retractor having a broad portion 26 and a hook 27. A tongue 22 of the tip 21 and a tongue 24 of a broad metal band 25 fit into opposite ends of a short piece of metal tubing 23.

Each of the tips 11 and 21 may have a metal core and a ceramic surface or each may be a single piece of ceramic.

Figure 3:
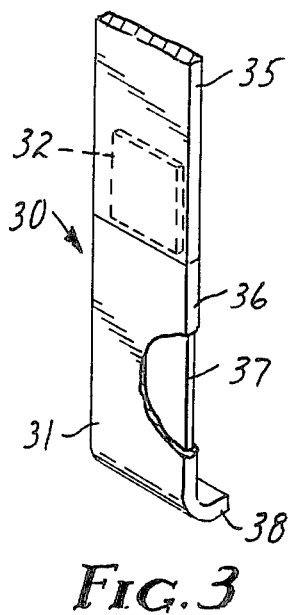
FIG. 3 is an isometric view, partly broken away, of a third surgical retractor of the invention.

The surgical retractor 30 of FIG. 3 has a tip 31 which has a rigid metal core 37 covered with a ceramic coating 36. The metal core 37 has a tongue 32 which has been swaged into a cavity in a broad, malleable metal band 35. A bend 38 at the extremity of the tip 31 helps to prevent retracted soft tissue from slipping out.

DESCRIPTION OF THE PREFERRED EMBODIMENTS

EXAMPLE 1

The surgical retractor 10 of FIG. 1 may be constructed as follows:
tip 11: annealed 304 soft stainless steel having a thickness of 1.0 mm, a width of 12 mm, a length of 20 mm, and a coating of zirconium oxide 0.1 mm in thickness.
tubing 13: annealed soft 304 stainless steel having a thickness of 0.25 mm.
band 15: annealed soft 304 stainless steel having a thickness of 1.0 mm.

EXAMPLE 2

In the surgical retractor 20 of FIG. 2, the tip 21 is 6 mm wide, its broad portion 26 is 12 mm long, and its hook 27 is about 4 mm in length.

EXAMPLE 3

The tip 31 of the surgical retractor 30 of FIG. 3 is 12 mm long, 6 mm wide, and its bend 38 extends about 1 mm from the adjacent broad face.

I claim:

1. Sterilizable surgical retractor, the tip of which is designed for insertion into an incision, wherein the improvement comprises:
   the electrical resistivity at the surface of the tip is at least $10^3$ ohms/cm$^2$;
   the thermal conductivity at the surface of the tip is not substantially greater than that of a typical ceramic; and
   the surface of the tip has a Rockwell C hardness of at least 55.

2. Sterilizable surgical retractor as defined in claim 1 wherein the electrical resistivity at the surface of the tip is at least $10^6$ ohms/cm$^2$.

3. Sterilizable surgical retractor as defined in claim 1 and including a broad metal band which is sufficiently malleable to be bent by hand to a desired shape while being sufficiently stiff to hold that shape against a retractile force applied to the other end of the band to pull the muscles and other tissue away from the center of an incision.

4. Sterilizable surgical retractor as defined in claim 3, the broad metal band of which is annealed soft stainless steel having a thickness of about 1 mm.

5. Sterilizable surgical retractor as defined in claim 1 wherein the tip comprises metal having a ceramic coating.

6. Sterilizable surgical retractor as defined in claim 5 wherein the ceramic coating is selected from aluminum oxide, zirconium oxide, aluminum silicate, and silicon nitride.

7. Sterilizable surgical retractor as defined in claim 6 wherein the ceramic coating has a thickness from about 0.05 to 1.0 mm.

8. Sterilizable surgical retractor as defined in claim 1 wherein wherein the tip comprises a piece of ceramic attached to the end of an otherwise conventional surgical retractor.

9. Sterilizable surgical retractor comprising a thin metal band, the tip of which is designed for insertion into an incision and is covered by a ceramic coating that has
   an electrical resistivity of at least $10^3$ ohms/cm$^2$;
   a thermal conductivity not substantially greater than that of a typical ceramic; and
   a Rockwell C hardness of at least 55.

10. Sterilizable surgical retractor as defined in claim 9 wherein the electrical resistivity at the surface of the tip is at least $10^6$ ohms/cm$^2$.

11. Sterilizable surgical retractor as defined in claim 9, the thin metal band of which is annealed soft stainless steel having a thickness of about 1 mm.

12. Sterilizable surgical retractor as defined in claim 11 wherein the ceramic coating is selected from aluminum oxide, zirconium oxide, aluminum silicate, and silicon nitride.

13. Sterilizable surgical retractor as defined in claim 12 wherein the ceramic coating has a thickness from about 0.05 to 1.0 mm.

14. Sterilizable surgical retractor comprising a thin metal band, to the tip of which is attached a piece of ceramic that has
   an electrical resistivity of at least $10^3$ ohms/cm$^2$;
   a thermal conductivity not substantially greater than that of a typical ceramic; and
   a Rockwell C hardness of at least 55.

15. Sterilizable surgical retractor as defined in claim 14 wherein the ceramic piece is selected from aluminum oxide, zirconium oxide, aluminum silicate, and silicon nitride.

* * * * *